(12) United States Patent
De Kock et al.

(10) Patent No.: US 11,712,556 B2
(45) Date of Patent: Aug. 1, 2023

(54) EXTENDABLE/RETRACTABLE ACTIVE FIXATION CRM LEAD TIP DESIGN FOR TURN COUNT CONSISTENCY

(71) Applicant: Cardiac Pacemakers, Inc., St Paul, MN (US)

(72) Inventors: Andrew L. De Kock, Ham Lake, MN (US); Lili Liu, Maple Grove, MN (US); Joel P. Grover, St Paul, MN (US); James Finley, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 460 days.

(21) Appl. No.: 16/722,440

(22) Filed: Dec. 20, 2019

(65) Prior Publication Data

US 2020/0197690 A1 Jun. 25, 2020

Related U.S. Application Data

(60) Provisional application No. 62/783,802, filed on Dec. 21, 2018.

(51) Int. Cl.
*A61N 1/04* (2006.01)
*A61N 1/39* (2006.01)
*A61N 1/05* (2006.01)

(52) U.S. Cl.
CPC ........ *A61N 1/0488* (2013.01); *A61N 1/0573* (2013.01); *A61N 1/3956* (2013.01)

(58) Field of Classification Search
CPC ........................... A61N 1/0488; A61N 1/0573
See application file for complete search history.

(56) References Cited

U.S. PATENT DOCUMENTS

| 5,837,006 A * | 11/1998 | Ocel ............. A61N 1/0573 607/127 |
| 2003/0069625 A1* | 4/2003 | Ley ............... A61N 1/0573 607/122 |
| 2013/0158641 A1* | 6/2013 | Foster ............. A61N 1/05 607/116 |

* cited by examiner

*Primary Examiner* — Alyssa M Alter
(74) *Attorney, Agent, or Firm* — Nelson Mullins Riley & Scarborough LLP (57) ABSTRACT

Various aspects of the present disclosure are directed toward apparatuses, systems, and methods that include an implantable lead having a terminal pin, a conductor member configured to rotate in response to rotation of the terminal pin and a coupler arranged within configured to interface with the conductor member and having a rear bearing surface contacting the inner wall of a housing.

14 Claims, 5 Drawing Sheets

EXTENDABLE/RETRACTABLE ACTIVE FIXATION CRM LEAD TIP DESIGN FOR TURN COUNT CONSISTENCY

CROSS-REFERENCE TO RELATED APPLICATION

This application claims priority to Provisional Application No. 62/783,802, filed Dec. 21, 2018, which is herein incorporated by reference in its entirety.

TECHNICAL FIELD

The present invention relates to implantable medical devices and relates more particularly to leads for cardiac rhythm management (CRM) systems.

BACKGROUND

Various types of medical electrical leads for use in cardiac rhythm management (CRM) and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site.

SUMMARY

In Example 1, an implantable lead includes a flexible insulative body having a proximal end and an opposite distal end, the body defining a longitudinal axis of the lead; a terminal pin arranged at a proximal end of the flexible insulative body and configured to rotate relative to the body; a conductor member disposed longitudinally within the body coupled to the terminal pin and configured to rotate in response to rotation of the terminal pin; a housing arranged within the flexible insulative body adjacent the distal end of the flexible insulative body and including an inner wall defining a cavity; a coupler arranged within the cavity of the housing including a proximal portion configured to interface with the conductor member and having a rear bearing surface contacting the inner wall of the housing, the coupler being configured to rotate in response to rotation of the conductor member; and a fixation helix coupled to a distal end of the coupler and configured to extend outwardly from the flexible insulative body in response to rotation of the coupler.

In Example 2, the implantable lead of Example 1, wherein the coupler includes a front bearing surface arranged within the housing contacting the inner wall of the housing.

In Example 3, the implantable lead of Example 2, wherein the rear bearing surface and the front bearing surface are configured to facilitate axial movement alignment of the coupler within the housing in response to rotation of the conductor member.

In Example 4, the implantable lead of Example 3, wherein the rear bearing surface and the front bearing surface are configured to lessen misalignment of the coupler relative to the longitudinal axis of the lead in response to rotation of the conductor member.

In Example 5, the implantable lead of Example 4, wherein the rear bearing surface and the front bearing surface are configured to maintain linear motion of the coupler within the housing in response to rotation of the conductor member.

In Example 6, the implantable lead of any one of Examples 2-5, wherein the housing includes a first portion having a first inner diameter and a second portion having a second inner diameter, and the second inner diameter is less than the first inner diameter.

In Example 7, the implantable lead of Example 6, wherein the first portion and the second portion are separable and configured to interface together.

In Example 8, the implantable lead of any one of Examples 6-7, wherein the second inner diameter is constant across a length of the second portion, and the rear bearing surface is configured to maintained within bounds of the second portion during linear motion of the coupler.

In Example 9, the implantable lead of any one of Examples 2-8, wherein the coupler includes an intermediate portion between the front bear surface and the rear bearing surface that is separate from the housing during linear motion of the coupler.

In Example 10, the implantable lead of any one of Examples 2-8, wherein the rear bearing surface includes a curvature about an outer diameter of the rear bearing surface.

In Example 11, the implantable lead of Example 10, wherein the curvature of the rear bearing surface is configured to minimize friction between the rear bearing surface and the housing during linear motion of the coupler.

In Example 12, the implantable lead of any one of Examples 2-11, wherein the rear bearing surface and the front bearing surface are configured to minimize torque loss between the rotation of the terminal pin and rotation of the fixation helix.

In Example 13, the implantable lead of Example 1, wherein the rear bearing surface includes a series of threads in an outer surface of the coupler.

In Example 14, the implantable lead of Example 13, wherein the housing is cooperatively threaded with the rear bearing surface to facilitate axial alignment of the coupler in response to rotation of the conductor member.

In Example 15, the implantable lead of Example 14, wherein the series of threads of the rear bearing surface and the housing facilitate linear motion of the coupler in response to rotation of the conductor member.

In Example 16, an implantable lead includes a flexible insulative body having a proximal end and an opposite distal end, the body defining a longitudinal axis of the lead; a terminal pin arranged at a proximal end of the flexible insulative body and configured to rotate relative to the body; a conductor member disposed longitudinally within the body coupled to the terminal pin and configured to rotate in response to rotation of the terminal pin; a housing arranged with the flexible insulative body adjacent the distal end of the flexible insulative body and including an inner wall defining a cavity; a coupler arranged within the cavity of the housing including a proximal portion configured to interface with the conductor member and having a front bearing surface and a rear bearing surface contacting the inner wall of the housing, the coupler being configured to rotate in response to rotation of the conductor member with the front bearing surface and the rear bearing surface being configured to facilitate linear motion of the coupler in alignment with the longitudinal axis of the lead; and a fixation helix coupled to a distal end of the coupler and configured to extend outwardly from the flexible insulative body in response to rotation of the coupler.

In Example 17, the implantable lead of Example 16, wherein the rear bearing surface and the front bearing surface are configured to facilitate axial movement alignment of the coupler within the housing in response to rotation of the conductor member.

In Example 18, the implantable lead of Example 17, wherein the rear bearing surface and the front bearing surface are configured to lessen misalignment of the coupler relative to the longitudinal axis of the lead in response to rotation of the conductor member.

In Example 19, the implantable lead of Example 18, wherein the rear bearing surface and the front bearing surface are configured to maintain linear motion of the coupler within the housing in response to rotation of the conductor member.

In Example 20, the implantable lead of Example 16, wherein the housing includes a first portion having a first inner diameter and a second portion having a second inner diameter, and the second inner diameter is less than the first inner diameter.

In Example 21, the implantable lead of Example 20, wherein the first portion and the second portion are separable and configured to interface together.

In Example 22, the implantable lead of Example 20, wherein the second inner diameter is constant across a length of the second portion, and the rear bearing surface is configured to maintained within bounds of the second portion during linear motion of the coupler.

In Example 23, the implantable lead of Example 16, wherein the coupler includes an intermediate portion between the front bearing surface and the rear bearing surface that is separate from the housing during linear motion of the coupler.

In Example 24, the implantable lead of Example 16, wherein the rear bearing surface includes a curvature about an outer diameter of the rear bearing surface.

In Example 25, the implantable lead of Example 24, wherein the curvature of the rear bearing surface is configured to minimize friction between the rear bearing surface and the housing during linear motion of the coupler.

In Example 26, the implantable lead of Example 16, wherein the rear bearing surface and the front bearing surface are configured to minimize torque loss between the rotation of the terminal pin and rotation of the fixation helix.

In Example 27, an implantable lead includes a flexible insulative body having a proximal end and an opposite distal end, the body defining a longitudinal axis of the lead; a terminal pin arranged at a proximal end of the flexible insulative body and configured to rotate relative to the body; a conductor member disposed longitudinally within the body coupled to the terminal pin and configured to rotate in response to rotation of the terminal pin; a housing arranged with the flexible insulative body adjacent the distal end of the flexible insulative body and including an inner wall defining a cavity; a coupler arranged within the cavity of the housing including a proximal portion configured to interface with the conductor member and having a threaded outer surface configured to interface with complimentary threads of the housing, the coupler being configured to rotate in response to rotation of the conductor member; and a fixation helix coupled a distal end of the coupler and configured to extend outwardly from the flexible insulative body in response to rotation of the coupler.

In Example 28, the implantable lead of Example 27, wherein the housing is cooperatively threaded with the threaded outer surface of the coupler to facilitate axial alignment of the coupler in response to rotation of the conductor member.

In Example 29, the implantable lead of Example 27, wherein the housing is cooperatively threaded with the threaded outer surface of the coupler to facilitate linear motion of the coupler in response to rotation of the conductor member.

In Example 30, a method includes arranging a lead adjacent a target location within a patient's heart, the lead including flexible insulative body having a proximal end and an opposite distal end, the body defining a longitudinal axis of the lead, a terminal pin arranged at a proximal end of the flexible insulative body, a conductor member disposed longitudinally within the body coupled to the terminal pin, a housing arranged with the flexible insulative body adjacent the distal end of the flexible insulative body and including an inner wall defining a cavity, a coupler arranged within the cavity of the housing including a proximal portion configured to interface with the conductor member and having a front bearing surface and a rear bearing surface contacting the inner wall of the housing, and a fixation helix coupled a distal end of the coupler; and rotating the terminal pin to rotate the conductor member to rotate the coupler with the front bearing surface and the rear bearing surface being configured to facilitate linear motion of the coupler in alignment with the longitudinal axis of the lead and extend the fixation helix extend outwardly from the flexible insulative body in response to rotation of the coupler.

In Example 31, the method of Example 30, wherein the rear bearing surface and the front bearing surface are configured to minimize torque loss between the rotation of the terminal pin and rotation of the fixation helix.

In Example 32, the method of Example 30, wherein the rear bearing surface and the front bearing surface are configured to facilitate axial movement alignment of the coupler within the housing in response to rotation of the conductor member.

In Example 33, the method of Example 32, wherein the rear bearing surface and the front bearing surface are configured to lessen misalignment of the coupler relative to the longitudinal axis of the lead in response to rotation of the conductor member.

In Example 34, the method of Example 33, wherein the rear bearing surface and the front bearing surface are configured to maintain linear motion of the coupler within the housing in response to rotation of the conductor member.

In Example 35, the method of Example 30, wherein the rear bearing surface includes a curvature about an outer diameter of the rear bearing surface.

While multiple instances are disclosed, still other instances of the present invention will become apparent to those skilled in the art from the following detailed description, which shows and describes illustrative instances of the invention. Accordingly, the drawings and detailed description are to be regarded as illustrative in nature and not restrictive.

While the invention is amenable to various modifications and alternative forms, specific instances have been shown by way of example in the drawings and are described in detail below. The intention, however, is not to limit the invention to the particular instances described. On the contrary, the invention is intended to cover all modifications, equivalents, and alternatives falling within the scope of the invention as defined by the appended claims.

DETAILED DESCRIPTION

Various aspects of the present disclosure are directed toward leads for stimulating a patient's heart. Leads may include a fixation mechanism, such as a fixation helix located at a distal end of the lead, to anchor the lead at a target location within the heart. The fixation helix may be extended and retracted via the proximal end of the lead by rotation of a terminal pin by a physician. Due to the length and flexibility, for example, of the lead and elements that connect the fixation helix and the terminal pin, the ability to extend and retract the fixation helix depends on multiple factors such as torque transmission of conductor, axial forces on conductor, friction between lead components, helix alignment, etc. Various aspects of the present disclosure are directed facilitating alignment and extension/retraction of the fixation helix. For example, the distal components are axially aligned, relative to a distal end of the lead. In addition, compression of the distal components may be controlled. Further, as a user rotates the terminal pin and torque is transmitted to the helix, the distal components discussed herein facilitate minimal binding of the helix and with minimal torque loss.

Figure 1:
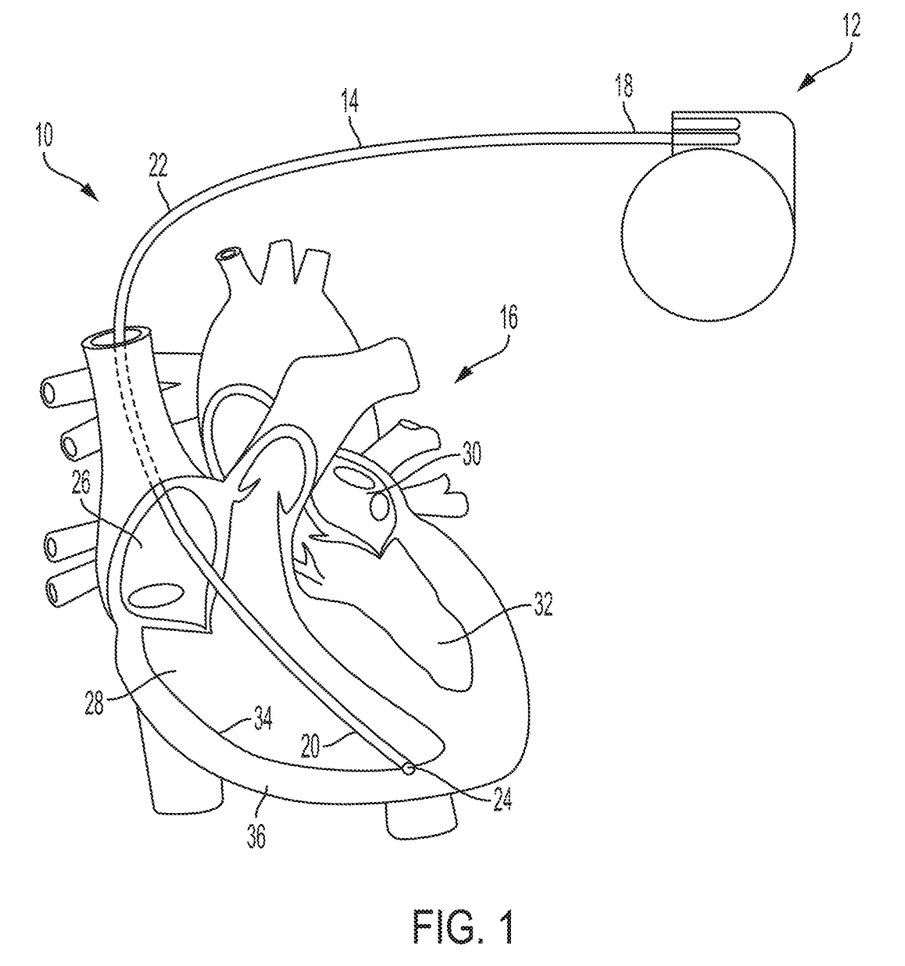
FIG. 1 is a perspective view of an example implantable cardiac rhythm management (CRM) system 10, in accordance with an embodiment.

FIG. 1 is a perspective view of an implantable cardiac rhythm management (CRM) system 10, in accordance with an embodiment. The CRM system 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body 22 extending from the proximal region 18 to the distal region 20. The proximal region 18 is coupled to the pulse generator 12 and the distal region 20 is coupled to the heart 16. The distal region 20 includes a fixation helix 24, which, as will be discussed in greater detail below, locates and/or secures the distal region 20 within the heart 16. As will be explained in detail below, the distal region 20 of the lead 14 includes configurations of the fixation helix 24 that provide improved tissue holding performance.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various instances, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities, e.g., a CRT-D device.

The lead body 22 can be made from any flexible, biocompatible materials suitable for lead construction. In various instances, the lead body 22 is made from a flexible, electrically insulative material. In one embodiment, the lead body 22 is made from silicone rubber. In another embodiment, the lead body 22 is made from polyurethane. In various instances, respective segments of the lead body 22 are made from different materials, so as to tailor the lead body characteristics to its intended clinical and operating environments. In various instances, the proximal and distal ends of the lead body 22 are made from different materials selected to provide desired functionalities.

As shown in FIG. 1, the heart 16 includes a right atrium 26, a right ventricle 28, a left atrium 30 and a left ventricle 32. It can be seen that the heart 16 includes an endothelial inner lining or endocardium 34 covering the myocardium 36. In some instances, as illustrated, the fixation helix 24, located at the distal region 20 of the lead, penetrates through the endocardium 34 and is imbedded within the myocardium 36. In one embodiment, the CRM system 10 includes a plurality of leads 14. For example, it may include a first lead 14 adapted to convey electrical signals between the pulse generator 12 and the right ventricle 28 and a second lead (not shown) adapted to convey electrical signals between the pulse generator 12 and the right atrium 26.

The fixation helix 24 penetrates the endocardium 34 of the right ventricle 28 and is embedded in the myocardium 36 of the heart 16. In some instances, the fixation helix 24 is electrically active and thus operates as a helical electrode for sensing the electrical activity of the heart 16 and/or applying a stimulating pulse to the right ventricle 28. In other instances, the fixation helix 24 is not electrically active. The fixation discussed in detail below may also operate as a helical electrode. Rather, in some instances, other components of the lead 14 are electrically active.

Figure 2:
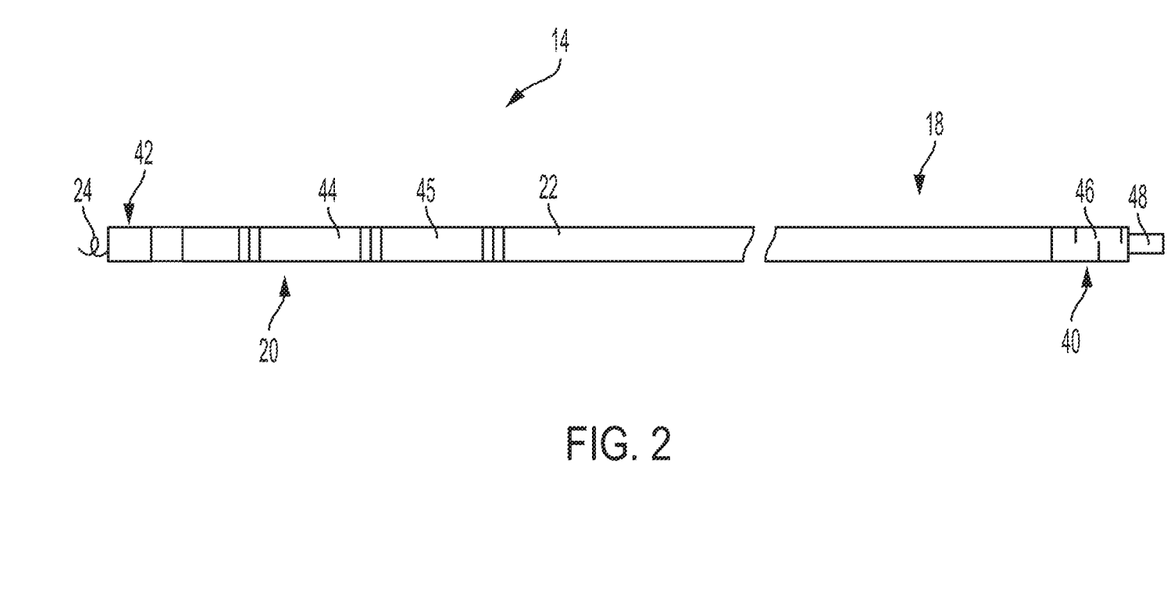
FIG. 2 is an illustration of an example lead including a fixation helix, in accordance with an embodiment.

FIG. 2 is an illustration of an example lead including a fixation helix, in accordance with an embodiment. The lead 14 includes a connector assembly 40 is disposed at or near the proximal region 18 of the lead 14 while a distal assembly 42 is disposed at or near the distal region 20 of the lead 14. Depending on the functional requirements of the CRM system 10 (e.g., as shown in FIG. 1) and the therapeutic needs of a patient, the distal region 20 may include one or more electrodes. In the illustrated embodiment, the distal region 20 includes a pair electrodes 44 and 45. The electrodes 44 and 45 may be coil electrodes that are configured as shocking electrodes for providing a defibrillation shock to the heart 16. In some instances, one or more of the coil electrodes 44 and 45 may act as low voltage pace or sense electrodes. In other instances, the electrodes 44 and 45 may be ring electrodes. The ring electrodes 44 and 45 may be configured as relatively low voltage pace/sense electrodes. In short, a wide range of electrode combinations may be incorporated into the lead 14 within the scope of the various instances of the present invention.

The connector assembly 40 includes a connector 46 and a terminal pin 48. The connector 46 is configured to be coupled to the lead body 22 and is configured to mechanically and electrically couple the lead 14 to a header on the pulse generator 12 (e.g., as shown in FIG. 1). In various instances, the terminal pin 48 extends proximally from the connector 46 and in some instances is coupled to a conductor member (as shown in detail in FIGS. 3-5) that extends longitudinally through the lead body 22 such that rotating the terminal pin 48 (relative to the lead body 22) causes the conductor member to rotate within the lead body 22. In some instances, the terminal pin 48 includes an aperture extending through in order to accommodate a guide wire or an insertion stylet.

Figure 3:
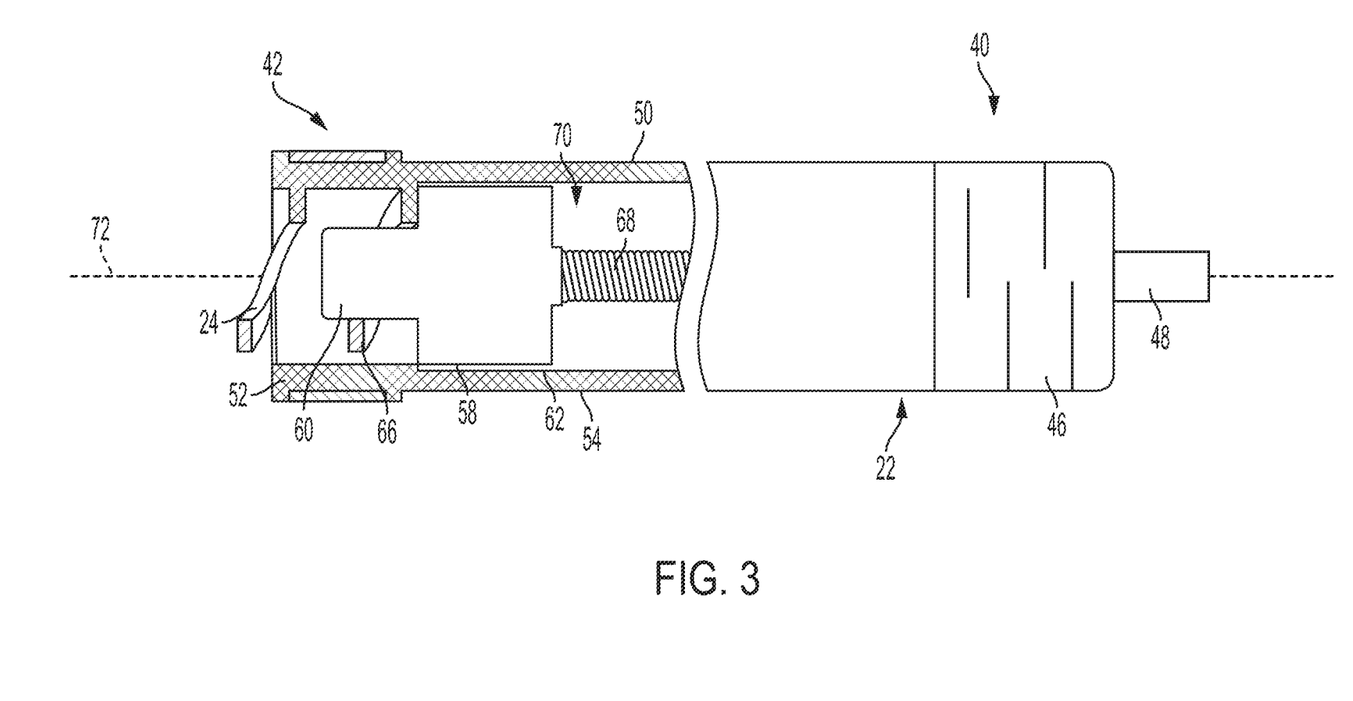
FIG. 3 is a cross-sectional illustration of an example lead including a fixation helix, in accordance with an embodiment.
Figure 4:
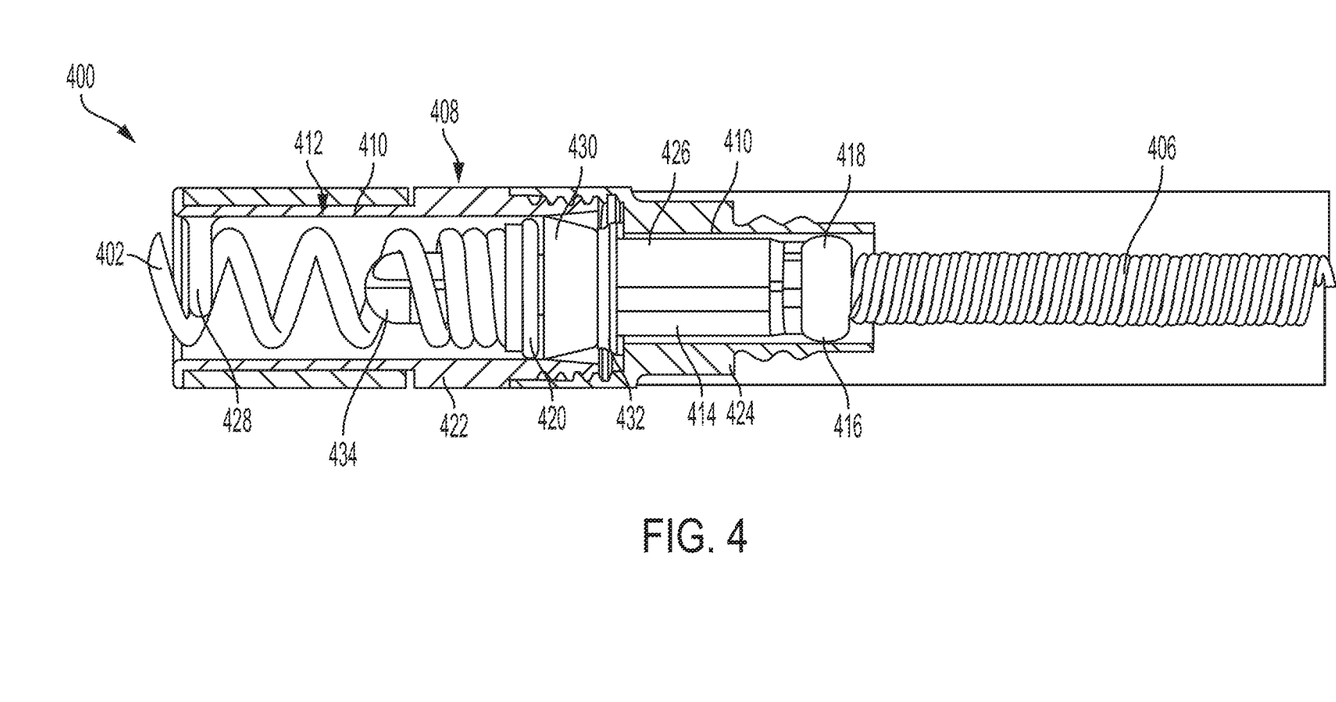
FIG. 4 is a cross-sectional illustration of a distal end portion of an example lead including a fixation helix, in accordance with an embodiment.
Figure 5:
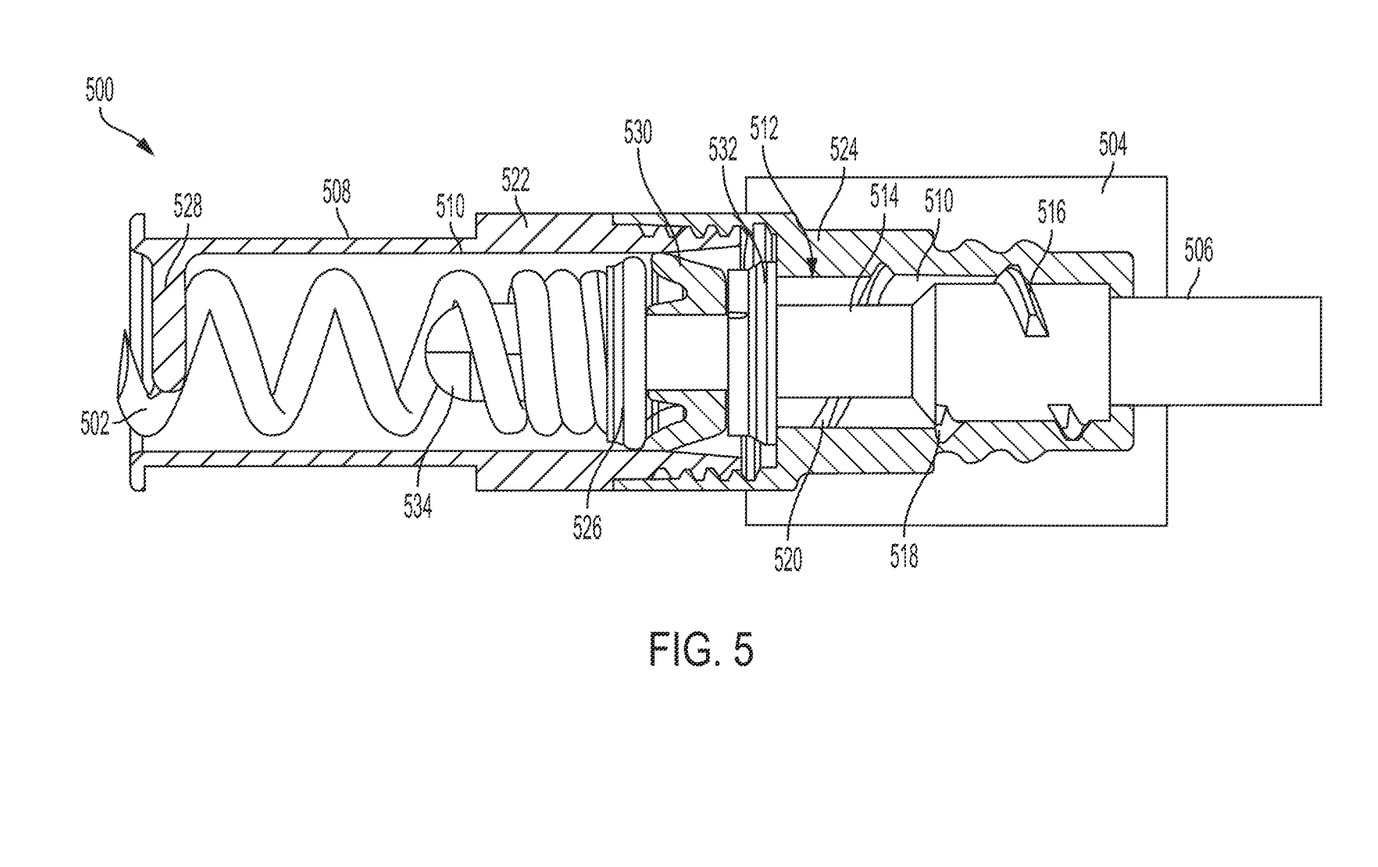
FIG. 5 is a cross-sectional illustration of a distal end portion of another example lead including a fixation helix, in accordance with an embodiment.

The distal assembly 42 includes a housing (as shown in FIGS. 3-5), within which the fixation helix 24 is at least partially disposed. In some instances, the housing includes or accommodates a mechanism that enables the fixation helix 24 to move distally and proximally relative to the housing 50. As noted above, the fixation helix 24 operates as an anchoring means for anchoring the distal region 20 of the lead 14 within the heart 16. In some instances, the fixation helix 24 is electrically active, and is also used as a helical pace/sense electrode. In some instances, the fixation helix 24 is made of an electrically conductive material such as Elgiloy, MP35N, nickel, tungsten, tantalum, iridium, platinum, titanium, palladium, stainless steel as well as alloys of any of these materials. In some instances, the fixation helix 24 is made of a non-electrically conductive material such as PES (polyethersulfone), polyurethane-based thermoplastics, ceramics, polypropylene and PEEK (polyetheretherketone).

FIG. 3 is a cross-sectional illustration of an example lead including a fixation helix, in accordance with an embodiment. The lead 14 may include a distal region 52 and a proximal region 54. In addition, the lead 14 may include a housing 50 arranged in the distal region 52 of the lead 14. The housing 50 may be relatively rigid or semi-rigid as compared to the lead 14. In some instances, the housing 50 may be made of an electrically conductive material such as Elgiloy, MP35N, nickel, tungsten, tantalum, iridium, platinum, titanium, palladium, stainless steel as well as alloys of any of these materials. In certain instances, the housing 50 is made of a non-electrically conductive material such as PES, polyurethane-based thermoplastics, ceramics, polypropylene and PEEK.

The distal assembly 42 includes a coupler 58 that has a distal portion 60 and a proximal portion 62. In some instances, the coupler 58 is formed of a metallic material and is configured to move longitudinally and/or rotationally with respect to the housing 50. In some instances, as illustrated, the distal portion 60 may have a relatively smaller diameter (relative to the proximal portion 62) in order to accommodate the fixation helix 24. While not illustrated, in some instances the proximal portion 62 is configured to accommodate a seal that provides a seal between the coupler 58 and the housing 50.

The fixation helix 24 has a proximal region 66 that is secured to the distal portion 60 of the coupler 58 using any suitable attachment technique. In some instances, the proximal region 66 of the fixation helix 24 is welded or soldered onto the distal portion 60 of the coupler 58. In certain instances, the fixation helix 24 may operate as a helical electrode.

As further shown, the lead 14 includes a conductor member 68 disposed within the lead body 22. The conductor member 68 has a proximal region (not visible) and a distal region 70. As shown, the distal region 70 is secured to the proximal portion 62 of the coupler 58, and the conductor member 68 extends proximally through the lead body 22 to the connector assembly 40. The proximal region of the conductor member 68 is coupled to the terminal pin 48 such that rotation of the terminal pin 48 causes the conductor member 68, and consequently, the coupler 58, to rotate.

As discussed herein, the lead 14 is an extendable/retractable lead. Thus, the housing 50 includes structure to convert rotational movement of the coupler 58 (and hence the fixation helix 24) relative to the housing 50 into translational movement of the coupler 58 (and hence the fixation helix 24) relative to the housing 50. The lead 14 can be considered as having a longitudinal axis 72. As shown in FIG. 3, the proximal portion 62 may be considered a rear bearing surface that contacts an inner wall of the housing 50. The proximal portion 62 contacting the housing 50 may facilitate linear motion of the coupler 58 to extend and retract the fixation helix 24 in alignment with the longitudinal axis 72. In instances where the proximal portion 62 does not contact the housing 50, the coupler 58 may tilt or misalign relative to the longitudinal axis 72, which in turn may cause binding or undesirable extension/retraction of the fixation helix 24. The proximal portion 62 contacting the housing 50, as discussed in further detail below, facilitates transmission of torque applied to the terminal pin 48 to the helix 24 with minimal binding of the helix 24 and with minimal torque loss.

FIG. 4 is a cross-sectional illustration of a distal end portion of an example lead 400 including a fixation helix 402, in accordance with an embodiment. The lead 400 includes a flexible insulative body 404 having a proximal end (e.g., as shown above in reference to FIGS. 1-3) and an opposite distal end as highlighted in FIG. 4. The body 404 defining a longitudinal axis of the lead 400. As also noted above with reference to FIGS. 1-3, the lead 400 may also include a terminal pin arranged at the proximal end of the flexible insulative body 404 that is configured to rotate relative to the flexible insulative body 404.

The lead 400 may also include a conductor member 406 that is disposed longitudinally within the body 404 and that is coupled to the terminal pin. The conductor member 406 may be configured to rotate in response to rotation of the terminal pin. As shown in FIG. 4, the lead 400 also includes a housing 408 arranged with the flexible insulative body 404 adjacent the distal end of the flexible insulative body 404 and including an inner surface 410 defining a cavity 412. The housing 408 may be arranged within the flexible insulative body 404 or extend distally from the body 404. A coupler 414 is arranged within the cavity 412 of the housing 408. The coupler 414 is configured to interface with the conductor member 406. In certain instances and as shown, a proximal portion 416 of the coupler 414 is configured to interface with the conductor member 406. The proximal portion 416 of the coupler 414 includes a rear bearing surface 418 that contacts the inner surface 410 of the housing 408. In certain instances and as shown in FIG. 4, the coupler 414 also includes a front bearing surface 420 that also contacts the inner surface 410 of the housing 408.

The front bearing surface 420 and the rear bearing surface 418 are configured to facilitate linear motion of the coupler 414. In certain instances, the front bearing surface 420 and the rear bearing surface 418 are configured to facilitate linear motion of the coupler 414 in alignment with the longitudinal axis of the lead 400. The body 404 may be flexible and in arranging the lead 400 at a target location, the body 404 may include one or more curvatures. Thus, the longitudinal axis of the lead 400 may be considered the longitudinal axis relative to a straight or linear portion of the lead 400 (e.g., the housing 408) or the longitudinal axis of the lead 400 in an unbent configuration.

In certain instances, the coupler 414 is configured to rotate in response to the rotation of the conductor member 406 with the rear bearing surface 418 and the front bearing surface 420 being configured to facilitate axial movement alignment of the coupler 414 within the housing 408 in response to rotation of the conductor member 406. The rear bearing surface 418 and the front bearing surface 420 maintain alignment within the housing 408 by contacting the inner surface 410 of the housing 408. The rear bearing surface 418 and the front bearing surface 420, for example, contacting the inner surface 410 of the housing 408 may lessen angling of the coupler 414 within the housing 408. Torque from the user rotating the terminal pin is transmitted along the conductor member 406 may attempt to torque and angle the coupler 414. The rear bearing surface 418 and the front bearing surface 420 contacting the inner surface 410 of the housing 408 may maintain alignment by not allowing the coupler 414 to angle in the housing 408.

In certain instances, the rear bearing surface 418 and the front bearing surface 420 are configured to lessen misalignment of the coupler 414 relative to the longitudinal axis of the lead 400 in response to rotation of the conductor member 406. As noted above, the rear bearing surface 418 and the front bearing surface 420 contacting the inner surface 410 of the housing 408 may lessen the ability of torque transmitted by the conductor member 406 to misalign the coupler 414. In addition, the rear bearing surface 418 and the front bearing surface 420 are configured to maintain linear motion of the coupler 414 within the housing 408 in response to rotation of the conductor member 406.

As shown in FIG. 4, the housing 408 includes a first portion 422 having a first inner diameter and a second portion 424 having a second inner diameter with the second inner diameter less than the first inner diameter. In certain instances, the first portion 422 and the second portion 424 may be separable and configured to interface together. In addition and as shown in FIG. 4, the second inner diameter is constant across a length of the second portion 424. The rear bearing surface 418 is configured to stay within bounds of the second portion 424 during linear motion of the coupler 414.

In certain instances, the coupler 414 includes an intermediate portion 426 between the front bearing surface 420 and the rear bearing surface 418 that is separated or includes a gap between the inner surface 410 of the housing 408 during linear motion of the coupler 414. The rear bearing surface 418 may include a curvature about an outer diameter of the rear bearing surface 418. In certain instances, the rear bearing surface 418 having the curvature minimizes friction between the rear bearing surface 418 and the housing 408 during linear motion of the coupler 414.

The rear bearing surface 418 and the front bearing surface 420 are configured to minimize torque loss between the rotation of the terminal pin and rotation of the fixation helix 402. The rear bearing surface 418 and the front bearing surface 420 maintaining alignment of the coupler 414 within the housing 408 may facilitate direct torque transmission from rotation of the terminal pin. In certain instances, the rear front bearing surface 418 may include a curvature about an outer diameter of the rear front bearing surface 418.

As a result of the rotation of the terminal pin (thereby rotating the conductor member 406 and the coupler 414), the coupler 414 may rotate the fixation helix 402, coupled to a distal end of the coupler 414, to extend the fixation helix 402 outwardly from the flexible insulative body 404. Rotation of the terminal pin in an opposite direction retracts the fixation helix 402. The housing 408 may include a drive cog 428 at the distal end to facilitate rotation of the fixation helix 402. In addition, the lead body may include a seal 430 between the front bearing surface 420 and a stop 432. The stop 432 may be a linear stop to stop rear motion of the coupler 414.

A curved surface 434 of the distal end of the coupler 414 minimizes friction when the curved surface 434 contacts the drive cog 428. In addition, the curved surface of the drive cog 428 may minimizes friction between the drive cog 428 and helix 402.

FIG. 5 is a cross-sectional illustration of a distal end portion of another example lead 500 including a fixation helix 502, in accordance with an embodiment. The lead 500 includes a flexible insulative body 504 having a proximal end (e.g., as shown above in reference to FIGS. 1-3) and an opposite distal end as highlighted in FIG. 5. The body 504 defines a longitudinal axis of the lead 500 (e.g., in an unbent configuration). As also noted above with reference to FIGS. 1-3, the lead 500 may also include a terminal pin arranged at the proximal end of the flexible insulative body 504 that is configured to rotate relative to the flexible insulative body 504.

The lead 500 may also include a conductor member 506 that is disposed longitudinally within the body 504 and that is coupled to the terminal pin. The conductor member 506 may be configured to rotate in response to rotation of the terminal pin. As shown in FIG. 4, the lead 500 also includes a housing 508 arranged with the flexible insulative body 504 adjacent the distal end of the flexible insulative body 504 and including an inner wall 510 defining a cavity 512. The housing 508 may be arranged within the flexible insulative body 504 or extend distally from the body 504. A coupler 514 is arranged within the cavity 512 of the housing 508. The coupler 514 is configured to interface with the conductor member 506. In certain instances and as shown, a proximal portion 516 of the coupler 514 is configured to interface with the conductor member 506. The proximal portion 516 of the coupler 514 includes a rear bearing surface 518 in the form of series of threads (or threaded outer surface) that contacts the inner wall 510 of the housing 508. The threaded outer surface 518 of the proximal portion 516 of the coupler 514 configured to interface with complimentary threads 520 of the housing 508.

In certain instances and as shown in FIG. 5, the coupler 514 also includes a front bearing surface 526 that also contacts the inner wall 510 of the housing 508. The front bearing surface 510 and the threaded outer surface 518 are configured to facilitate linear motion of the coupler 514 and rotate the coupler 514 in response to rotation of the conductor member 506. In addition, the threaded outer surface 518 and the cooperatively threaded housing 508 facilitate axial alignment of the coupler 514 in response to rotation of the conductor member 506.

The housing 508, which may be a unitary structure, includes a first portion 522 having a first inner diameter and a second portion 524 having a second inner diameter with the second inner diameter is less than the first inner diameter. In certain instances, the first portion 522 and the second portion 524 may be separable and configured to interface together. In addition and as shown in FIG. 5, the second portion 524 includes the threads 520 of the housing 508. The threaded outer surface 518 of the proximal portion 516 is configured to stay within bounds of the threads 520 of the housing 508.

As a result of the rotation of the terminal pin (thereby rotating the conductor member 506 and the coupler 514), the coupler 514 may rotate the fixation helix 502, coupled to a distal end of the coupler 514, to extend the fixation helix 502 outwardly from the flexible insulative body 504. Rotation of the terminal pin in an opposite direction retracts the fixation helix 502. The body 504 may include a drive cog 528 at the distal end to facilitate rotation of the fixation helix 502. The threaded outer surface 518 of the proximal portion 516 may stabilize the coupler 514 such that the drive cog 528 is optional (e.g., the threaded outer surface 518 act as the drive cog to ensure that the fixation helix 502 rotates and actuates linearly). In addition, the lead body may include a seal 530 between the front bearing surface 526 and a stop 532. The stop 532 may be a linear stop to stop rear motion of the coupler 514. In certain instances, the threaded outer surface 518 and threads 520 prevent axial compression or tension of the conductor member 506 onto the fixation helix 502.

Preventing axial compression or tension of the conductor member 506 being passed to the fixation helix 502 facilitates the fixation helix 502 rotating and actuating linearly and minimizes binding.

A curved surface 534 of the distal end of the coupler 514 minimizes friction when the curved surface 534 contacts the drive cog 528. In addition, the curved surface of the drive cog 528 may minimizes friction between the drive cog 528 and helix 402.

Various modifications and additions can be made to the exemplary instances discussed without departing from the scope of the present invention. For example, while the instances described above refer to particular features, the scope of this invention also includes instances having different combinations of features and instances that do not include all of the described features. Accordingly, the scope of the present invention is intended to embrace all such alternatives, modifications, and variations as fall within the scope of the claims, together with all equivalents thereof.

We claim:

1. An implantable lead comprising:
   a flexible insulative body having a proximal end and an opposite distal end, the body defining a longitudinal axis of the lead;
   a terminal pin arranged at a proximal end of the flexible insulative body and configured to rotate relative to the body;
   a conductor member disposed longitudinally within the body coupled to the terminal pin and configured to rotate in response to rotation of the terminal pin;
   a housing arranged with the flexible insulative body adjacent the distal end of the flexible insulative body and including an inner wall defining a cavity;
   a coupler arranged within the cavity of the housing including a proximal portion configured to interface with the conductor member and having a front bearing surface, a rear bearing surface, and an intermediate portion between the front bearing surface and the rear bearing surface, the front bearing surface and the rear bearing surface each contacting the inner wall of the housing, and a gap defined between the intermediate portion and the inner surface of the housing, the coupler being configured to rotate and translate relative to the housing in response to rotation of the conductor member with the front bearing surface and the rear bearing surface being configured to facilitate linear motion of the coupler in alignment with the longitudinal axis of the lead, and the rear bearing surface including a curvature about an outer diameter of the rear bearing surface; and
   a fixation helix coupled to a distal end of the coupler and configured to extend outwardly from the flexible insulative body in response to rotation of the coupler.

2. The implantable lead of claim 1, wherein the rear bearing surface and the front bearing surface are configured to facilitate axial movement alignment of the coupler within the housing in response to rotation of the conductor member.

3. The implantable lead of claim 2, wherein the rear bearing surface and the front bearing surface are configured to lessen misalignment of the coupler relative to the longitudinal axis of the lead in response to rotation of the conductor member.

4. The implantable lead of claim 3, wherein the rear bearing surface and the front bearing surface are configured to maintain linear motion of the coupler within the housing in response to rotation of the conductor member.

5. The implantable lead of claim 1, wherein the housing includes a first portion having a first inner diameter and a second portion having a second inner diameter, and the second inner diameter is less than the first inner diameter.

6. The implantable lead of claim 5, wherein the first portion and the second portion are separable and configured to interface together.

7. The implantable lead of claim 5, wherein the second inner diameter is constant across a length of the second portion, and the rear bearing surface is configured to maintained within bounds of the second portion during linear motion of the coupler.

8. The implantable lead of claim 1, wherein the curvature of the rear bearing surface is configured to minimize friction between the rear bearing surface and the housing during linear motion of the coupler.

9. The implantable lead of claim 1, wherein the rear bearing surface and the front bearing surface are configured to minimize torque loss between the rotation of the terminal pin and rotation of the fixation helix.

10. A method comprising:
    arranging a lead adjacent a target location within a patient's heart, the lead including flexible insulative body having a proximal end and an opposite distal end, the body defining a longitudinal axis of the lead, a terminal pin arranged at a proximal end of the flexible insulative body, a conductor member disposed longitudinally within the body coupled to the terminal pin, a housing arranged with the flexible insulative body adjacent the distal end of the flexible insulative body and including an inner wall defining a cavity, a coupler arranged within the cavity of the housing including a proximal portion configured to interface with the conductor member and having a front bearing surface, a rear bearing surface, and an intermediate portion between the front bearing surface and the rear bearing surface, the front bearing surface and the rear bearing surface each contacting the inner wall of the housing, and a gap defined between the intermediate portion and the inner surface of the housing, and the rear bearing surface including a curvature about an outer diameter of the rear bearing surface, and a fixation helix coupled a distal end of the coupler; and
    rotating the terminal pin to rotate the conductor member to cause rotational and translational movement of the coupler relative to the housing with the front bearing surface and the rear bearing surface being configured to facilitate linear motion of the coupler in alignment with the longitudinal axis of the lead and extend the fixation helix extend outwardly from the flexible insulative body in response to rotation of the coupler.

11. The method of claim 10, wherein the rear bearing surface and the front bearing surface are configured to minimize torque loss between the rotation of the terminal pin and rotation of the fixation helix.

12. The method of claim 10, wherein the rear bearing surface and the front bearing surface are configured to facilitate axial movement alignment of the coupler within the housing in response to rotation of the conductor member.

13. The method of claim 12, wherein the rear bearing surface and the front bearing surface are configured to lessen misalignment of the coupler relative to the longitudinal axis of the lead in response to rotation of the conductor member.

14. The method of claim 13, wherein the rear bearing surface and the front bearing surface are configured to maintain linear motion of the coupler within the housing in response to rotation of the conductor member.

\* \* \* \* \*